United States Patent
Orfao De Matos Correia E Vale

(10) Patent No.: US 9,746,472 B2
(45) Date of Patent: Aug. 29, 2017

(54) METHODS AND KITS FOR THE DETECTION OF CANCER INFILTRATION OF THE CENTRAL NERVOUS SYSTEM

(75) Inventor: José Alberto Orfao De Matos Correia E Vale, Salamanca (ES)

(73) Assignee: UNIVERSIDAD DE SALAMANCA, Salamanca (ES)

( * ) Notice: Subject to any disclaimer, the term of this patent is extended or adjusted under 35 U.S.C. 154(b) by 0 days.

(21) Appl. No.: 13/557,543

(22) Filed: Jul. 25, 2012

(65) Prior Publication Data

US 2013/0029868 A1  Jan. 31, 2013

Related U.S. Application Data

(60) Provisional application No. 61/511,633, filed on Jul. 26, 2011.

(51) Int. Cl.
*G01N 33/574* (2006.01)

(52) U.S. Cl.
CPC . *G01N 33/57407* (2013.01); *G01N 33/57488* (2013.01)

(58) Field of Classification Search
None
See application file for complete search history.

(56) References Cited

U.S. PATENT DOCUMENTS

2006/0024744 A1* 2/2006 Mills .................... G01N 33/564 435/7.1
2012/0142001 A1* 6/2012 Skog ........................ C07H 1/08 435/6.12

FOREIGN PATENT DOCUMENTS

WO  WO/2011/046842  *  4/2011  ....... G01N 33/57488

OTHER PUBLICATIONS

Quijano et al, Journal of Clinical Oncology, vol. 27, No. 9, 2009.*
Wang et al, Experimental Hematology & Oncology 2012, 1:36.*
Kersten et al., Blood 1996, 87: 1985-1989.
Murase et al., Cancer Lett. 1998, 132: 181-186.
Chamberlain et al., Sem. Oncol. 2009, 36(4): s35-s45.
Subira et al., HIV Med. 2005, 6: 21-26.
Quijano et al., J. Clin. Oncol. 2009; 27(9): 1462-1469.
Bromberg et al., J. Neurology 2007, 68: 1674-1679.
Hedge et al., Blood 2005, 105: 496-502.
Sancho et al., Eur. J. Haematol. 2010, 85: 321-328.
Hildebrandt et al., BMC Cancer 2007, 7: 185.
Schroers et al., Eur. J. Haematol. 2010, 85: 520-528.
Roy et al., J. Clin. Oncol. 2008, 26(1): 96-105.
Kersten, et al., "Elevation of cerebrospinal fluid soluble CD27 levels in patients with meningeal localization of lymphoid malignancies [published erratum appears in Blood Oct. 1, 1996; 88(7):2818]", Blood, (1996), pp. 1985-1989.
Kraan, et al., "Flow Cytometric Immunophenotyping of Cerebrospinal Fluid", Current Protocols in Cytometry, (Jul. 2008), pp. 6.25.1-6.25.16.
Murase, et al., "Increased levels of CSF soluble CD27 in patients with primary central nervous system lymphoma", Cancer Letters 132, (1998), pp. 181-186.

* cited by examiner

*Primary Examiner* — Catherine S Hibbert
(74) *Attorney, Agent, or Firm* — Blakely Sokoloff Taylor & Zafman LLP

(57) ABSTRACT

This invention relates to methods to detect the presence of cancer infiltration of the Central Nervous System (CNS) based on the detection of soluble proteins, preferably, in cerebrospinal fluid samples and vitreous fluid. The invention also relates to kits to perform the methods of the invention.

6 Claims, No Drawings

METHODS AND KITS FOR THE DETECTION OF CANCER INFILTRATION OF THE CENTRAL NERVOUS SYSTEM

CROSS REFERENCE TO RELATED APPLICATION

This application claims the benefit of U.S. Provisional Patent Application Ser. No. 61/511,633, filed Jul. 26, 2011, the disclosure of which is incorporated herein by reference.

FIELD OF THE INVENTION

This invention relates to the field of medical diagnostics. It provides methods and kits to detect the presence of cancer infiltration of the Central Nervous System (CNS), preferably, but not limited to, cerebrospinal fluid samples.

BACKGROUND OF THE INVENTION

For decades, cytomorphological analysis of cytospin preparations of cerebrospinal fluid (CSF) has been considered the gold standard for the diagnosis of leptomeningeal involvement in both primary and secondary central nervous system lymphomas. In addition, it contributes to the diagnosis of other hematological and non-hematological tumors that are localized in the central nervous system (CNS). Although such conventional cytological analyses of CSF are associated with a high specificity for identification of CNS disease in lymphoma and other cancer patients, evidence has also accumulated about its limited sensitivity with a frequency of between 20% and 60% false negative results (Chamberlain et al, Sem Oncol 2009; 36: s35-s45). More recently, multiple studies have shown that flow cytometry immunophenotyping of cells present in CSF samples provides a similarly specific but much more sensitive approach for the detection of leptomeningeal disease in aggressive B-cell non-Hodgkin lymphomas (B-NHL) and in other lymphoid and myeloid malignancies, as well as in solid tumors (Subira et al HIV Med 2005, 6: 21-26; Quijano et al J Clin Oncol, 2009; 27: 1462-I 469;.Bromberg et al J Neurology 2007; 68: 1674-1679; Hedge et al Blood 2005, 105: 496-502). Among lymphoma cases, such increased sensitivity is associated with a dismal patient outcome due to increased CNS and systemic relapse rates (Hedge et al, Blood 2005, 105: 496-502; Sancho et al, Eur J Haematol 2010). Despite the increased sensitivity of multiparameter flow cytometry versus conventional cytological procedures, still a significant proportion of patients who show no neoplastic B-cells or other tumor cells in their CSF, either by flow cytometry or by conventional cytology, display neurological symptoms highly suspicious of CNS involvement by the lymphoma or other type of tumor with or without results compatible with a diagnosis of tumor involvement of the CNS by magnetic resonance imaging (MRI) and other imaging techniques. In parallel, still a significant fraction of all CNS relapses that occur among e.g. aggressive B-NHL involve patients who showed flow cytometry negative (FCM-)/conventional cytology (CC-) CSF. Altogether, these results point out the need for more sensitive approaches to detect CNS involvement among aggressive B-NHL and also other hematological and non-hematological tumors.

In this regard, it has been suggested that in such cases, false negative results of FCM and CC could be due to occurrence of parenchymal infiltration by the tumor cells, in the absence of leptomeningeal involvement. Although, definitive demonstration of this hypothesis still remains to be established, it could be speculated that while in cases showing leptomeningeal involvement, lymphoma cells could easily and rapidly reach CSF allowing their detection by FCM and/or CC, in cases where CNS involvement is restricted to parenchymal localizations, tumor cells would not easily spread to the cerebroespinal fluid (or the vitrous fluid). However, under such circumstances it would be expected that due to an increased cellular turn-over, an increased release of soluble tumor cell proteins, RNA, DNA and other cell components by living or dying tumor cells, could make their levels into the CSF (and/or the vitrous fluid) detectable. In fact, a few studies have been previously reported in which the amount of specific cellular immune response-associated (but not tumor related) proteins, e.g., CD27 (Kersten et al, Blood 1996, 87: 1985-1989; Murase et al, Cancer Lett 1998, 132: 181-186), free light chains (Hildebrandt et al BMC cancer, 2007, 7: 185; Schroers et al Eur J Haematol 2010, 85: 236-242) and antithrombin (Roy et al, J Clin Oncol 2008, 26: 96-105) are detected in CSF from patients with multiple CNS diseases, despite such measurements, provided diagnostically inefficient results. Of note, none of these proteins are tumor-specific and they could not be directly linked with tumor cell death and/or active secretion by tumor cells.

DETAILED DESCRIPTION OF THE INVENTION

This invention provides a method to determine the presence of one or more tumor cell-derived proteins or their specific DNA and RNA sequences that are released by cells into the extracellular compartment in a form that is soluble in a fluid and/or quantify their amounts in a biological central nervous system sample, preferably in a cerebrospinal fluid sample, to evaluate the existence of infiltration of the central nervous system by cancer cells in a patient, the method comprising the steps of:
  a. providing a biological central nervous system sample from the subject,
  b. capturing one or more tumor-cell-associated proteins or peptide fragments derived from said proteins or their specific DNA and RNA sequences, into a solid platform composed of one or more ELISA plate wells, immunobeads or flat-surface array spots, through a set of one or more probes or to a set of soluble probes, and
  c. detecting and/or quantifying said one or more tumor cell proteins, or peptide fragments derived from said proteins or their DNA or RNA specific sequences.

The methods are based on detecting tumor cell-specific and/or associated proteins and their coding DNA and RNA molecules, preferably in cerebrospinal fluid samples. Such proteins, RNA and DNA molecules are released into the extracellular compartment due to cell death, cell lysis or active secretion and release by tumor cells. To detect such proteins and their fragments, one or multiple pairs of antibodies or other probes specific for an amino acid sequence of said tumor proteins and their fragments are used in conventional and multiplexed immuno-analysis "sandwich" assays, while for RNA and DNA molecules conventional PCR-based molecular techniques are employed. These assays include conventional ELISA, other single or multiplexed flow cytometry immunobead assays or flat-surface spot arrays. They can be used alone or in combination with conventional cytomorphological, immunocytochemical, flow cytometry immunophenotyping and molecular diagnostic approaches for the simultaneous detection of the presence of soluble proteins, DNA and/or RNA, as well as of entire tumor cells. Such assays may be applied to the diagnostic screening of CNS tumor disease in both patients suspected of having a tumor or diagnosed with a tumor, as well as for the evaluation of treatment effectiveness in cerebrospinal fluid (CSF) samples from patients diagnosed with CNS disease due to infiltration by lymphoma, leukemia or a solid tumor. The assay may also include one or more immunobeads, ELISA plate wells or flat-surface microarray spots for simultaneous determination of the presence of blood infiltration through the detection and quantification of red-cell proteins (e.g. haemoglobin and glycosylated haemoglobin) in combination or not with the measurement of non-nucleated red cells.

Thus, the first aspect of the present invention refers to a method to detect the presence of infiltration of the central nervous system by cancer cells in a biological central nervous system sample of a subject comprising determining the presence of at least a tumor cell-derived soluble protein or their specific DNA and RNA sequences comprising the steps of:

a. providing a biological central nervous system sample from the subject,
b. capturing one or more tumor-cell-associated proteins or peptide fragments derived from said proteins or their specific DNA and RNA sequences, into a solid platform composed of one or more ELISA plate wells, immunobeads or flat-surface array spots, through a set of one or more probes or to a set of soluble probes, and
c. detecting and/or quantifying said one or more tumor cell proteins, or peptide fragments derived from said proteins or their DNA or RNA specific sequences.

Said proteins and protein fragments, DNA and RNA sequences may be studied on fresh cerebrospinal fluid samples or they can be investigated in preserved, fixed and frozen samples, directly or after being treated with protease inhibitors.

The tumor to be detected may be an aggressive B- T- or NK-cell non-Hodgkin lymphoma, a low grade B-, T- or NK-cell non-Hodgkin lymphoma, a chronic B- and T-cell lymphoid leukemia, an acute myeloblastic leukemia, an acute lymphoblastic leukemia/lymphoma, a Hodgkin lymphoma, a malignant plasma cell disorder, a glioma, a meningioma, a neuroblastoma, a medulloblastoma, and metastasis of breast cancer, lung cancer, prostate cancer, colon cancer or any other type of cancer.

The protein of the present invention is the product of the expression of a nucleotide sequence. This nucleotide sequence can be any RNA as for example, but not limited to, messenger RNA (mRNA), or a fragment thereof. This nucleotide sequence can also be complementary DNA (cDNA) or a fragment thereof. The cDNA is DNA complementary to an mRNA or is also the nucleotide sequence comprising exons from a genomic sequence but not introns, that is, the coding sequence. The transcription of both genomic sequence of a gene and its cDNA encode for the same mRNA and, therefore, encode for the same protein. In the present invention, it is also possible to detect any RNA or any DNA, or a fragment thereof, instead of the protein or at the same time as the protein or proteins of interest or their peptide fragments.

Preferably, the proteins to be identified and quantified, may vary according to the type of cancer and can be selected from the following set of human proteins or combinations of them: CD19, CD20, CD21, CD23, CD24, CD3, TCRVbeta, TCRValfa, TCRVgamma, CD34, CD10, CD79a, CD22, BCR/ABL, TEL-AML1, MLL-AF4, CD117, MPO, Tryptase, CD13, CD33, CD15, CD14, CD36, CD64, lysozyme, EGFR, CK8, CK18, CK19, CK20, EpCAM, Her2/neu and PSA. More preferably, the proteins to be identified and quantified can be selected from the following set of human proteins or combinations of them: CD19, CD20, CD21, CD23 and CD24 in case of B-NHL and chronic B-cell leukemias: CD3. TCRVbeta, TCRValfa, TCRVgamma and TCRVbeta in case of T-cell NHL and chronic lymphoid leukemias; CD34, CD19, CD10, CD79a, CD22, BCR/ABL, TEL-AML1, MLL- AF4, in case of B-cell precursor acute lymphoblastic leukaemia and B-cell precursor Lymphoblastic lymphoma; CD34, CD 117, MPO, Tryptase, CD13, CD33, CD15, CD14, CD36, CD64, lysozyme, Pml-Rara, Amll-eto in case of acute myeloblastic leukaemia and other myeloid malignancies; EGFR and GFAP for gliomas; CK8, CK18, CK19, CK20, EpCAM and Her2/neu for breast cancer; PSA for prostate cancer. The above mentioned proteins are referred in the present invention as to the "proteins of the invention".

Said proteins to be identified may correspond to full length proteins or to peptide fragments of said proteins derived from their degradation by proteases. To detect and/or quantify the proteins of the present invention, it is sufficient to detect one or more fragments of said protein because the fragment is a constituent of the amino acidic sequence and structure of the protein. Simultaneous detection of two or more distinct full length proteins, one protein and one or more fragments of said proteins or just fragments of two or more distinct proteins may be used.

Said proteins may correspond to intracellular proteins (for example, cytoplasmic proteins, organelle proteins and nuclear proteins), to membrane bound cellular proteins, or combinations of both; they may be structural proteins, transcription factors. fusion proteins derived from chromosomal translocations, idiotypic immunoglobulins and idiotypic T-cell receptor molecules, mutated proteins, functional receptors, adhesion molecules and any kind of tumor-specific or tumour associated proteins.

Step (c) of the method refers to the detection and the quantification of the proteins of the present invention or to its detection or to its quantification.

In a preferred embodiment of this invention, said proteins or their peptide-fragments RNA and DNA specific sequences can be detected and/or quantified by flow cytometry immunobead assays in which two or more bead populations, each specific for a distinct protein or protein fragment or DNA or RNA sequence specific of said protein or protein fragment, or of multiple protein fragments, DNA or RNA sequences specific of said protein fragments, are simultaneously incubated in sequential steps with the sample and a fluorescently-conjugated secondary antibody or nucleic acid probe, PNA or LNA molecule, and measured in the flow cytometer.

In another embodiment of this invention, said proteins and their fragments are detected by electrophoretic chromatography, microarray based immunobead assays and other immunoassays.

Said immunoassays are biochemical tests that measure the concentration of a substance in a biological liquid using the reaction of an antibody or antibodies to its antigen, or any other probe to is aminoacid sequence ligand. The assay takes advantage of the specific binding of an antibody to its antigen. Detecting the quantity of antibody or antigen can be achieved by a variety of methods. One of the most common methods is to label either the antigen/ligand or antibody/probe. The label may comprise, but is not limited to, an enzyme, radioisotopes (radioimmunoassay), including stable isotopes, magnetic labels (magnetic immunoassay) or fluorescence, and also other techniques including agglutination, nephelometry, turbidimetry or Western Blot. Heterogeneous immunoassays can be competitive or non-competitive. The immunoassay can be competitive: the response will be inversely proportional to the concentration of antigen in the sample, or can be non-competitive (also referred to as the "sandwich assay"): the results are directly proportional to the concentration of the antigen. An immunoassay technique that can be used in the present invention is the Enzyme-Linked ImmunoSorbent Assay (ELISA).

In the solid platforms, pairs of antibodies specific for said full length proteins or their fragments are used to anchor and detect the presence of the protein.

In a preferred embodiment of this invention, said proteins are detected on the surface of immunobeads simultaneously with cerebrospinal fluid cells or vitreous fluid cells by flow cytometry, image cytometry, laser scanning cytometry or any other cytometry technique.

In another embodiment of this invention, said proteins are detected on the surface of immunobeads simultaneously with cell derived mRNA, miRNA or DNA using conventional techniques based on products amplified by polymerase chain reaction amplification of nucleic acid sequences.

The detection and/or quantification of any protein of the invention or any combination thereof can be carried out by combining any of the previous techniques. The protein can be detected by evaluating its presence or absence, or quantifying its amount. The detection can be carried out by the specific recognition of any fragment thereof by means of any probe and/or any antibody. Also the detected protein of the invention can be quantified so that it serves as reference for comparing these data with standard values to find any significant deviation.

In another embodiment of this invention, said tumor-associated proteins are detected and/or quantified simultaneously or in parallel with red cell specific proteins to evaluate the potential existence of blood contamination of cerebrospinal fluid and vitrous fluid samples, and its levels.

Based on the methods described above, specific kits for the detection of cerebrospinal fluid infiltration by cancer cells or vitrous fluid infiltration by tumor cells, can be devised and built. As an example, a kit comprising pairs of anti-CD19 and anti-CD21 or of anti-CD19 and anti-CD24 reagents or of anti-CD19 and anti-CD20 reagents, can be used to detect infiltration by tumor B-cells in aggressive B-cell non-Hodgkin's lymphomas, such as Burkitt lymphoma and diffuse large B-cell lymphoma. In another example, it comprises anti-CD3, anti-TCRVbeta, anti-TCR-Valfa, anti-TCRVgamma antibody reagents or any possible combination of these reagents. In another example, it comprises antibodies directed against the CD34, CD19, CD10, CD79a, CD22, BCR/ABL, TEL-AML1 and MLL-AF4 proteins or any combination thereof. In another example, anti-CD34, anti-CD117, anti-MPO, anti-Tryptase, anti-CD13, anti-CD33, anti-CD15, anti-CD14, anti-CD36, anti-CD64, anti-lysozyme or any combination of these antibody reagents, are used. In another example, anti-EGFR and anti-GFAP alone, in combination or in combination with other proteins associated with glioma cells are used. In other examples, antibodies specific for the CK8, CK18, CK19, CK20, EpCAM and Her2/neu and PSA proteins are used. All such examples are illustrative but not limiting examples.

Thus, a second aspect of the present invention refers to a kit for the detection of cerebrospinal fluid infiltration by cancer cells comprising at least a probe to detect any one of the proteins of the invention or their specific DNA and RNA sequences.

A further preferred embodiment refers to a kit, wherein the probes are attached to a solid support. This solid support preferably comprises beads (more preferably, inmuno-beads), a gel (e.g., agarose or polyacylamide gel), or any array-type solid matrix such as a slide made of distinct materials, such as glass with or without a gold-covered surface.

In another preferred embodiment, the probes are antibodies used to recognize the protein of the present invention, or a fragment thereof. The antibodies can be monoclonal or polyclonal.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice oldie invention. The following examples are provided by way of illustration and are not intended to be limiting of the present invention.

EXAMPLES

The following two examples provide a description and are of an illustrative and non-limiting character, of some of the assays and operating conditions claimed in the list of claims given below, such two examples referring to the detection of tumor cells in a cerebrospinal fluid sample and a vitreous fluid sample, each obtained from a distinct group of patients, which based on the symptoms they presented with, are suspicious of suffering from a central nervous system tumor of unknown subtype and a primary ocular tumor of unknown subtype, respectively.

Example 1

Quantification Assay of Soluble Tumour-Associated Proteins and Protein Fragments by Flow Cytometry Cerebrospinal fluid samples (between 2 and 10 mL) were obtained by lumbar puncture from 10 patients with high suspicion of suffering from a central nervous system tumor, specifically from either a primary central nervous system B-cell lymphoma or a glioma, after informed consent was given by each subject. Each sample was directly obtained in tubes containing TRANSFIX™ (Transfix tubes, Immunostep SL, Salamanca, Spain). Once obtained, the tube was centrifuged at 540 g for 5 min (room temperature) to sediment the cells; then, the supernatants were obtained and freezed at −80° C. Next, 100 microliters of each of the supernatants from each sample, were sequentially thawed and incubated (1 hour at room temperature) with an array of beads of capture, formed by six populations of beads whose surface had been previously covered by specific antibodies, each population being covered with a distinct antibody direct against epitopes of proteins derived from distinct types of tumor cells including B-cells and glioma cells, i.e., CD19, CD20, CD21, CD22, CD24, GFAP, and with control beads directed to the capture and identification of proteins usually absent in cerebrospinal fluid samples—negative control; mouse CD3—and proteins present in known amounts—positive control; e.g. albumin—(7$^{th}$ and 8$^{th}$ bead populations). Simultaneously (or immediately after this incubation period) a panel of second paired antibodies directed against distinct epitopes of all the above listed proteins—i.e. CD19, CD20, CD21, CD22, CD24, GFAP—all conjugated to the same fluorochrome (e.g. phycoerythrin) was added. When samples for which said panel of second antibodies was incubated separately from the first incubation of the sample with the immunobeads covered with antibodies, the second incubation was performed after adding 4 mL of phosphate buffered saline (PBS; pH=7.4), performing a centrifugation step at 540 g for 5 min and adding 100 microleters of PBS. With this step, those proteins subjected to study linked with their corresponding beads (or microspheres), were revealed. Then each sample was measured in a conventional flow cytometer capable of measuring 4 distinct fluorescences. The distinct bead populations were distinguished among them based on their different predefined amounts of green (Alexa488) fluorescence; after gating on each bead population, the specific phycoerythrin-associated fluorescence of each of the gated bead populations, reflecting the amount of each bead-associated protein, were then evaluated.

Information on the relative and absolute abundance of each of the proteins of interest in the sample was obtained by comparing the phycoerythrin fluorescence levels of each of the different populations of beads with the fluorescence levels of the same beads incubated with varying, pre-established increasing amounts of the same proteins, which had been processed and read in a flow cytometer exactly under the same conditions as the beads incubated with the cerebrospinal fluid samples.

For the analysis of the populations of beads, a computer program known by the skilled in the art, as for instance, INFINICYT™ software (Cytognos SL, Salamanca, Spain), was used. The information provided in the measures is both qualitative (presence vs absence of detectable protein) and quantitative allowing to evaluate the amount of protein per unit of volume of sample in terms of e.g. ng/mL.

Example 2

Quantification Assay of Soluble Tumor-Associated Proteins and Protein Fragments using an ELISA Enzyme-Linked Immunoassay Vitreous fluid samples (between 0.2 and 1.5 mL) were obtained by intraocular puncture from 10 patients with high suspicion of suffering from a central nervous system tumor, such as a primary occular lymphoma, after informed consent was given by each subject. Each sample was directly obtained in tubes containing culture media (RPMI 1640, Sigma, St Louis, Mo., USA). Once obtained, the tube was centrifuged at 540 g for 5 min (room temperature) to sediment the cells; then, the supernants were obtained and freezed at −80° C. Next, 100 microliters of each of the supernatants from each sample, were sequentially thawed and incubated (3 hours at room temperature) by triplicate in a 96-well plastic plate (Becton/Dickinson, New Jersey, N.J., USA) which had been previously coated with an anti-CD19 antibody. In parallel, different amounts of CD19 (0, 10, 20, 50, 100, 250, 500 and 1,000 ng in 100 microliters) were added by triplicate to other wells of the same plate to build a calibration curve. After this incubation, the plate wells were emptied and washed three times with distilled water. Then, a sencond anti-CD19 antibody directed against a different epitope of the CD19 molecule conjugated with horseradish peroxidase (HRP) in 100 microliters of phosphate buffered saline (PBS; pH=7.4) was added to each well and incubated for 2 hours. After this incubation, an HRP substrate was added and the plate incubated for 10 minutes in dark at room temperature. Immediately following this incubation period, 50 microliters/well of a sulphuric acid solution was added to stop the peroxidase reaction with the substrate. Then, the plate was read (optical density obtained through the enzymatic reaction) in a conventional ELISA plate reader equipped with the appropriate optical filters.

Information about the abundance of CD19 was calculated by plotting the optical density obtained for each sample (mean of the triplicate wells) against a standard curve built with the results (mean optical density of triplicate measurements) obtained for those wells to which known amounts of the CD19 protein was added (0, 10, 20, 50, 100, 250, 500 and 1,000 ng in 100 microliters), and that were processed in parallel with the patient samples analyzed.

What is claimed is:

1. A method to detect the presence of infiltration of the central nervous system by cancer cells in a biological central nervous system sample of a subject suspected of having cancer comprising determining the presence of a soluble protein CD19 comprising the steps of:
   a. providing a biological central nervous system sample from the subject, wherein the sample is suspected to comprise the soluble protein CD19,
   b. capturing the soluble protein CD19 of the sample of step (a), into a solid platform comprising at least an ELISA plate well, an immunobead or a flat-surface array spot, through a set of at least one probe specific for the soluble protein CD19, by placing in contact the sample with said at least one labeled probe linked to said solid platform, and
   c. detecting the presence of tumor infiltration of the central nervous system by detecting and/or quantifying the specific binding of the soluble protein CD19 of step (b) to at least one labeled probe;
   wherein
   the presence of infiltration means that the subject has a cancer selected from the group of an aggressive B-cell non-Hodgkin lymphoma, a low-grade B-cell non-Hodgkin lymphoma, a chronic B-cell lymphoid leukemia or a glioma infiltrating the CNS,
   the method further comprises detecting at least one of the soluble proteins selected from the group consisting of CD21, CD24, and glial fibrillary acid protein (GFAP), and
   the soluble protein CD19 is detected on the surface of immunobeads simultaneously with cerebrospinal fluid cells or vitreous fluid cells by cytometry.

2. The method according to claim 1, wherein the sample is a cerebrospinal fluid or vitreous fluid sample.

3. The method according to claim 1, wherein the sample is selected from preserved, fixed and frozen samples.

4. The method according to claim 1, wherein the sample is provided directly or after being treated with protease inhibitors.

5. A method for the evaluation of treatment effectiveness in patients diagnosed with CNS disease due to infiltration by lymphoma, leukemia or a solid tumor, comprising
   (i) administering to said patient a treatment for a CNS disease due to infiltration by lymphoma, leukemia or a solid tumor, and (ii) determining the presence of a soluble protein CD19, in a cerebrospinal fluid sample from said patient by the specific binding of said soluble protein CD19, and at least one labeled probe; wherein the absence of infiltration means that the treatment has been effective, the method further comprises detecting at least one of the soluble proteins selected from the group consisting of CD21, CD24, and glial fibrillary acid protein (GFAP), and the soluble protein CD19 is detected on the surface of immunobeads simultaneously with cerebrospinal fluid cells or vitreous fluid cells by cytometry.

6. The method according to claim 1, wherein the cytometry technique is flow cytometry, image cytometry or laser scanning cytometry.

* * * * *